United States Patent
Bright et al.

(10) Patent No.: US 10,588,772 B1
(45) Date of Patent: Mar. 17, 2020

(54) THERAPEUTIC BANDAGE/DRESSING/COVERING FOR HUMAN PENIS FITTED WITH CATHETER

(71) Applicants: Patrick Francis Bright, Los Angeles, CA (US); Robert M. Freed, Ojai, CA (US)

(72) Inventors: Patrick Francis Bright, Los Angeles, CA (US); Robert M. Freed, Ojai, CA (US)

( * ) Notice: Subject to any disclaimer, the term of this patent is extended or adjusted under 35 U.S.C. 154(b) by 0 days.

(21) Appl. No.: 15/934,675

(22) Filed: Mar. 23, 2018

(51) Int. Cl.
| A61M 1/00 | (2006.01) |
| A61F 5/30 | (2006.01) |
| A61M 25/02 | (2006.01) |
| A61M 25/06 | (2006.01) |
| A61M 25/00 | (2006.01) |
| A61M 27/00 | (2006.01) |

(52) U.S. Cl.
CPC ............... *A61F 5/30* (2013.01); *A61M 25/02* (2013.01); *A61M 25/0017* (2013.01); *A61M 27/008* (2013.01); *A61M 2025/0213* (2013.01); *A61M 2025/0681* (2013.01)

(58) Field of Classification Search
CPC .......... A61M 25/02; A61M 2025/0213; A61M 25/0017; A61M 27/008; A61M 2025/0681; A61F 5/30
USPC ....................................................... 604/313
See application file for complete search history.

(56) References Cited

U.S. PATENT DOCUMENTS

| 4,062,363 | A | * | 12/1977 | Bonner, Jr. | ........ A61M 25/0111 604/171 |
| 4,284,079 | A | * | 8/1981 | Adair | ...................... A61F 5/453 600/573 |
| 4,710,169 | A | * | 12/1987 | Christopher | .......... A61M 25/04 128/DIG. 25 |
| 5,242,398 | A | * | 9/1993 | Knoll | ................. A61M 25/0111 604/101.05 |
| 5,527,293 | A | * | 6/1996 | Zamierowski | .......... A61F 5/453 128/898 |
| 5,630,429 | A | * | 5/1997 | Dann | .................... A61F 2/0009 128/885 |
| 2007/0142794 | A1 | * | 6/2007 | Bester, Jr. | ............... A61F 5/453 604/349 |
| 2011/0230851 | A1 | * | 9/2011 | Kay | ........................ A61F 5/453 604/352 |
| 2012/0071717 | A1 | * | 3/2012 | Podolski | ................ A61B 1/126 600/109 |
| 2016/0128873 | A1 | * | 5/2016 | Martin | .............. A61F 13/00042 604/360 |

* cited by examiner

*Primary Examiner* — Andrew J Mensh
(74) *Attorney, Agent, or Firm* — Patrick Bright

(57) ABSTRACT

A therapeutic bandage/dressing/covering for use with a human penis fitted with a catheter that extends from a human's bladder through, and beyond the opening from the penis glans, is placed over the distal end of the penis, including the glans, and onto the surface of the catheter where the catheter protrudes from the glans. The covering surface that lies against the skin of the penis, penis glans, and the distal opening in the penis, may be padded, flexible or, rigid, and, optionally, medicated and/or lubricated, to minimize skin abrasion and promote cleanliness/sterility of the glans, the contiguous penis shaft, and other delicate penile tissues.

8 Claims, 6 Drawing Sheets

THERAPEUTIC BANDAGE/DRESSING/COVERING FOR HUMAN PENIS FITTED WITH CATHETER

Therapeutic coverings that may be placed over, or partly inside of, a human penis fitted with a catheter that extends from a human's bladder through, and beyond the urinary meatus. These coverings provide comfort, cleanliness, and sterility to the vulnerable/sensitive interface where the catheter emerges/protrudes from the urinary meatus.

These coverings, in a first group of embodiments, may be rigid or flexible, and may be one-piece, and wrap over, and, preferably, around the distal end of the penis. Once in place, these coverings cover the interface between the catheter and the urinary meatus/glans, and may serve to stabilize the junction between the urethral meatus and the catheter. The covering surfaces that are in contact with penile and glans tissues may be soft, non-abrasive, and may be lubricated, impregnated with antiseptic, germicidal or bacteriostatic agents, and/or padded to promote comfort, and minimize tissue damage.

In a second group of embodiments, the coverings may be rigid or flexible, and may be one-piece. A covering embodiment from this second group is adapted to/configured to wrap around, and generally conform to, the catheter external surface, and, when in place, may extend through the urethral meatus inside the urethra a distance of up to about 8 cm. A covering embodiment from the second group tapers at the end that fits inside the urethra to a narrow, generally tubular shape such that it can fit inside of the urethral meatus and urethra.

When in place inside the urethra, a covering embodiment from the second group may lie between the external surface of the catheter, and the internal surface of the urethra, thereby cushioning this interface, and reducing abrasion to the inner surface of the urethra.

In some cases, a covering from the first group of embodiments may be used with a covering from the second group of embodiments. When used with a first covering, a second covering may wrap over the first covering. Whether used alone or with the first covering, a second covering may serve to stabilize the junction between the urethral meatus and the catheter.

In some embodiments, these coverings may be made of woven fabric, lined with padding, preferably made of gauze or other soft cushioning, on surfaces that will lie against penile tissues with the coverings in place. Alternatively, these coverings could be made as molded tubular polymer pieces. These tissue-engaging surfaces may be coated/impregnated with lubricants such as lanolin or glycerine, and/or with antiseptic, germicidal or bacteriostatic agents.

In some embodiments, the coverings may have a thickness in the range of about 1 mm to about 5 mm, a length in the range of about 10 cm to about 130 cm, and width(s) in the range of about 7 cm to about 10 cm.

A rigid, relatively inflexible embodiment of the covering may be thicker than a flexible embodiment, with the external surface of the covering formed from plastic or other rigid material and the surface interfacing with the penis covered with padding such as gauze.

In some embodiments, these coverings may be formed as a substantially planar, flexible/supple, two-sided product having a first side and a second side. The first side, second side, or both, may include a soft, non-abrasive lubricated surface that is optionally coated/impregnated with lubricants such as lanolin or glycerine, and/or with antiseptic, germicidal or bacteriostatic agents. The coverings may be formed as one or more rectangular, square portions, but may also be formed in other shapes, such as curvilinear or triangular.

Some embodiments may include a first portion connected to a second portion by a neck portion that is positioned between said first portion and said second portion. The neck portion, and the first and second portions may be of sufficient size and appropriate shape to cover a human penis fitted with a catheter that extends from the bladder of a human through said human's urethra and beyond the opening in the glans of the penis.

Where the neck portion, or other portion, of the covering, is placed over the location where a catheter extends beyond the opening in the glans of the penis, the covering surface in contact with this location may provide a high degree of cushioning and of soothing lubricant.

DESCRIPTION OF THE DRAWINGS

Exemplary embodiments of the invention appear in the drawings, and are described in the following detailed description of the drawings, in which.

DETAILED DESCRIPTION OF THE DRAWINGS

Figure 1:
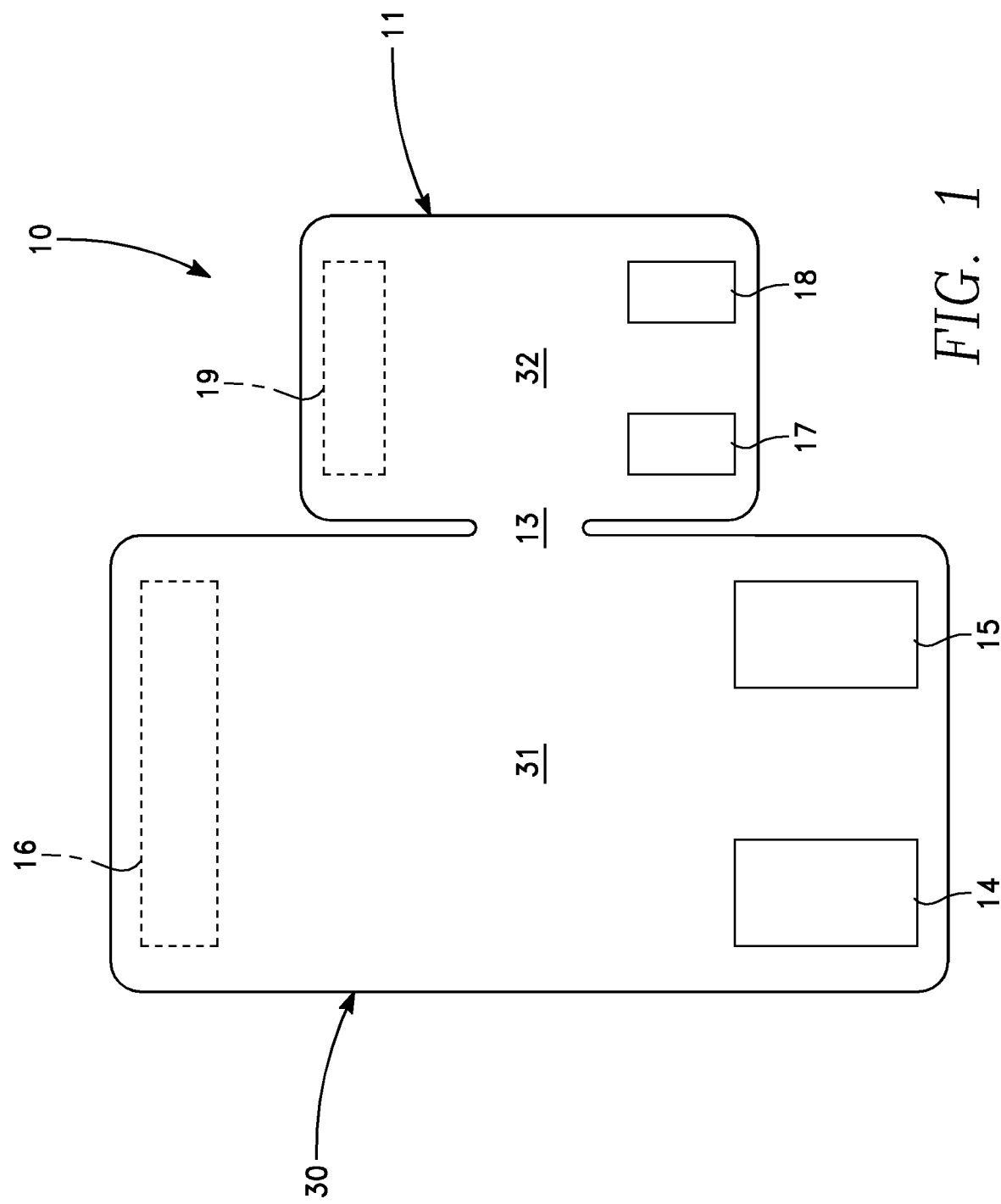
FIG. 1 is a plan view of a first, exemplary embodiment of therapeutic coverings that may be placed over/around a human penis fitted with a catheter that extends from a human's bladder through, and beyond the opening from the penis glans.
Figure 3:
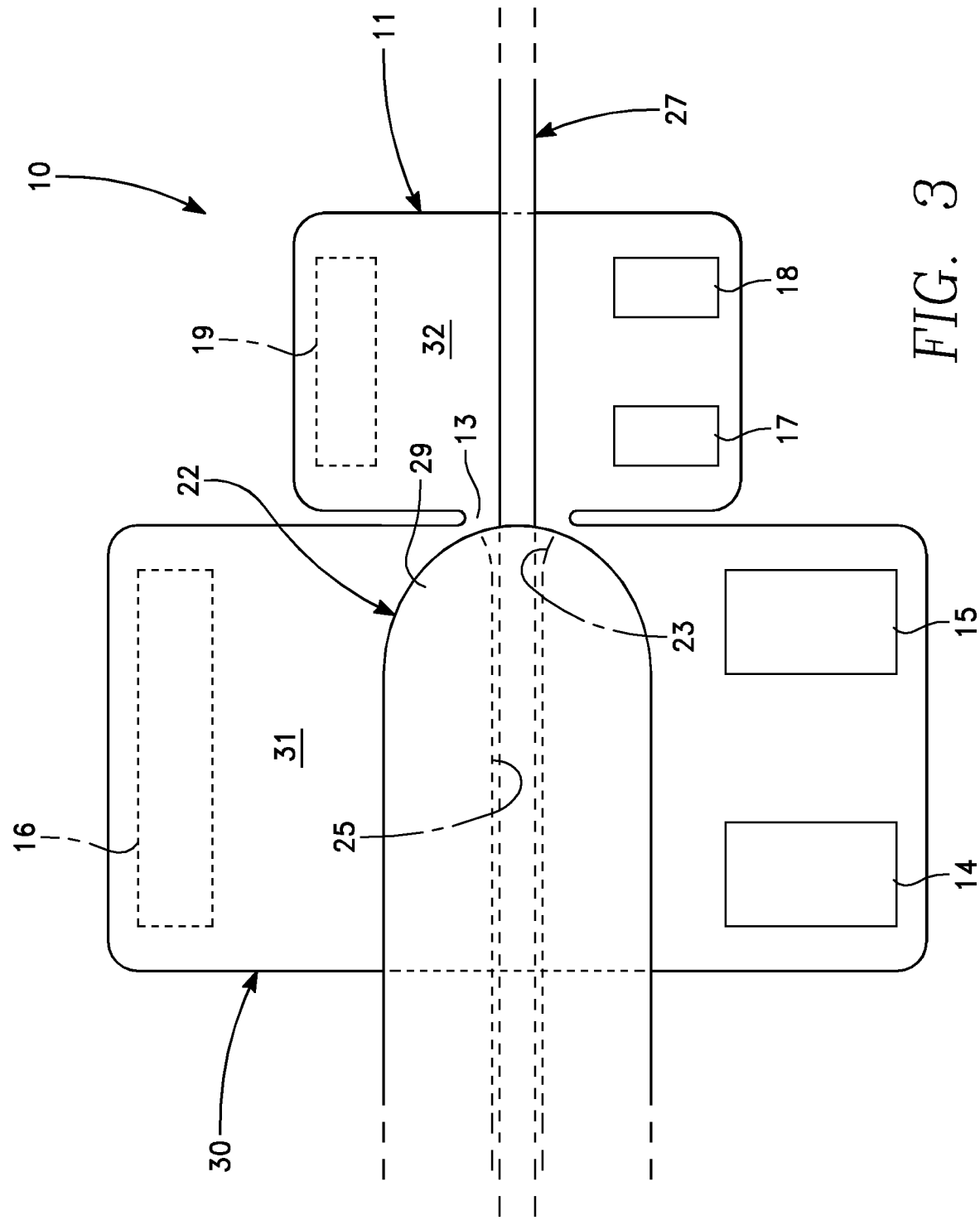
FIG. 3 is a side elevation view of the covering of FIG. 1 placed alongside a human penis fitted with a catheter that extends from a human's bladder through, and beyond the urethral meatus.

FIGS. 1 and 3 show a plan view of a first, exemplary embodiment of a therapeutic covering 10 that may be placed over a human penis 22 fitted with a catheter 27 that extends from a human's bladder (not shown) through, and beyond the urethral meatus 23 in the penis glans 29. One-piece covering 10 includes a larger, flat, generally square/rectangular proximal portion 30 joined to smaller, generally flat, distal square/rectangular portion 11 at junction 13. Inner surfaces 31 and 32 of portions 30 and 11 are soft, padded and, optionally, coated or impregnated with lubricant(s) and/or disinfectants over at least some of the areas that will be in contact with penile tissues when/while covering 10 is in place on penis 22.

Covering 10 also includes complementary fasteners 14/15/16 on portion 30, and 17/18/19 on portion 11. When covering 10 is wrapped over/around penis 22, complementary fasteners 14/15 on portion 30 engage fastener 16, and fasteners 17/18 engage fastener 19 on portion 11 to hold covering 10 in place over/around penis 22. Portion 13 of covering 10 covers the interface between penis opening 23 and catheter 27 where catheter 27 protrudes from penis opening 23. Portion 30 covers penis 22 from opening 23 proximally toward the junction of the penis and the groin of the wearer.

Figure 6:
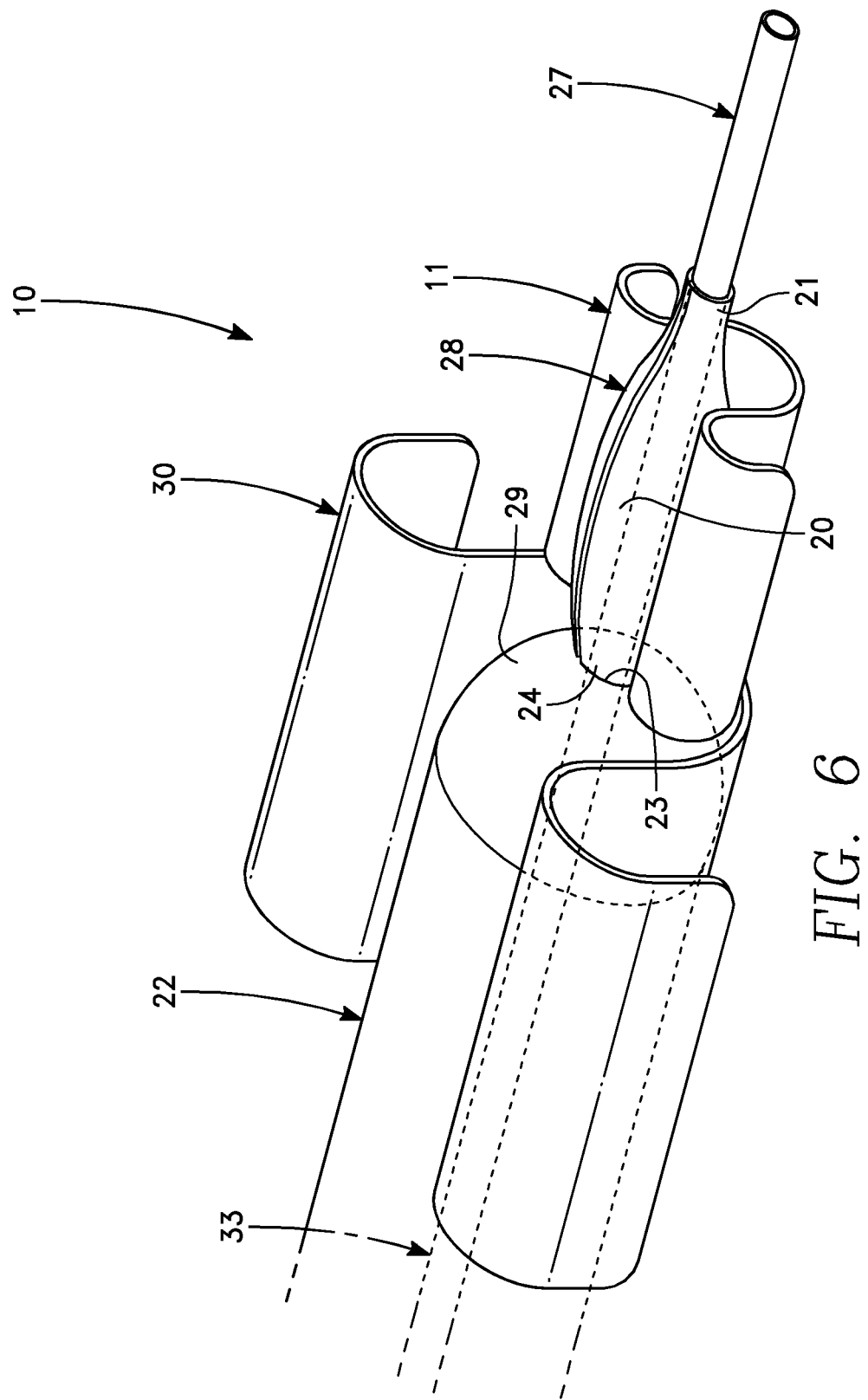
FIG. 6 is a perspective view of the covering of FIGS. 1 and 3, shown partially wrapped around a human penis fitted with a catheter.

FIG. 6 shows covering 10 partially wrapped around penis 22, and around urethral meatus 23.

Figure 2:
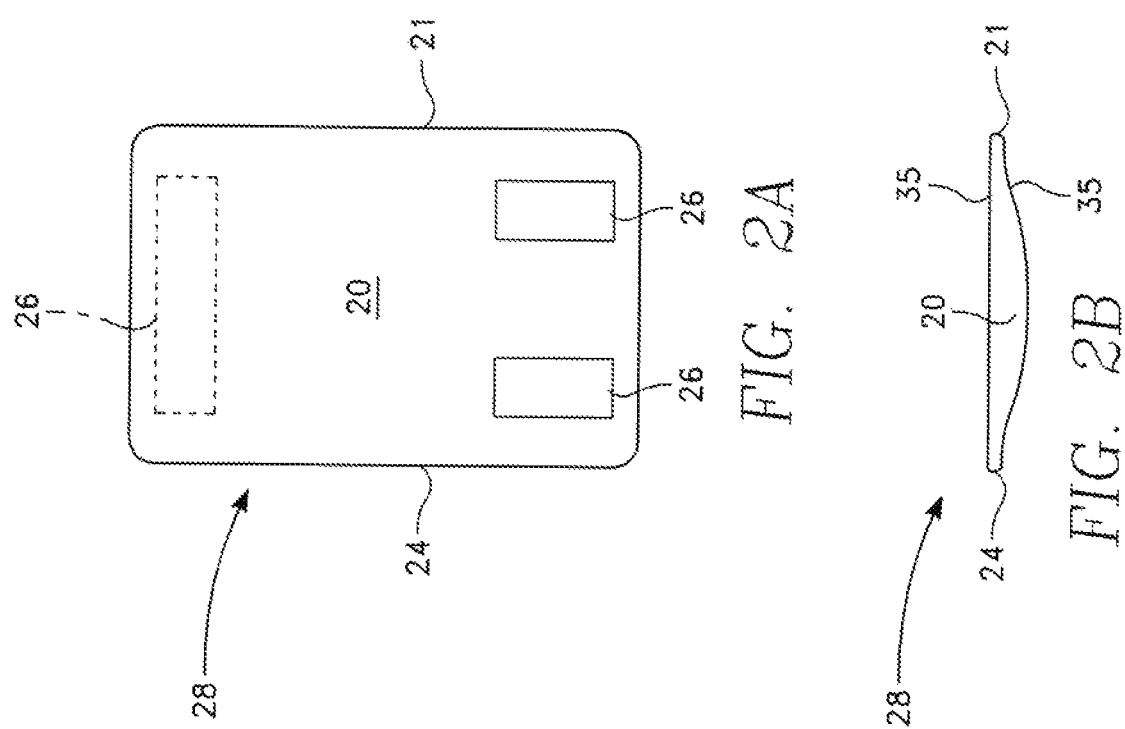
FIGS. 2A and 2B are plan and end views of a second, exemplary embodiment of therapeutic coverings that may be placed over, and/or partly inside of, a human penis fitted with such a catheter.
Figure 4:
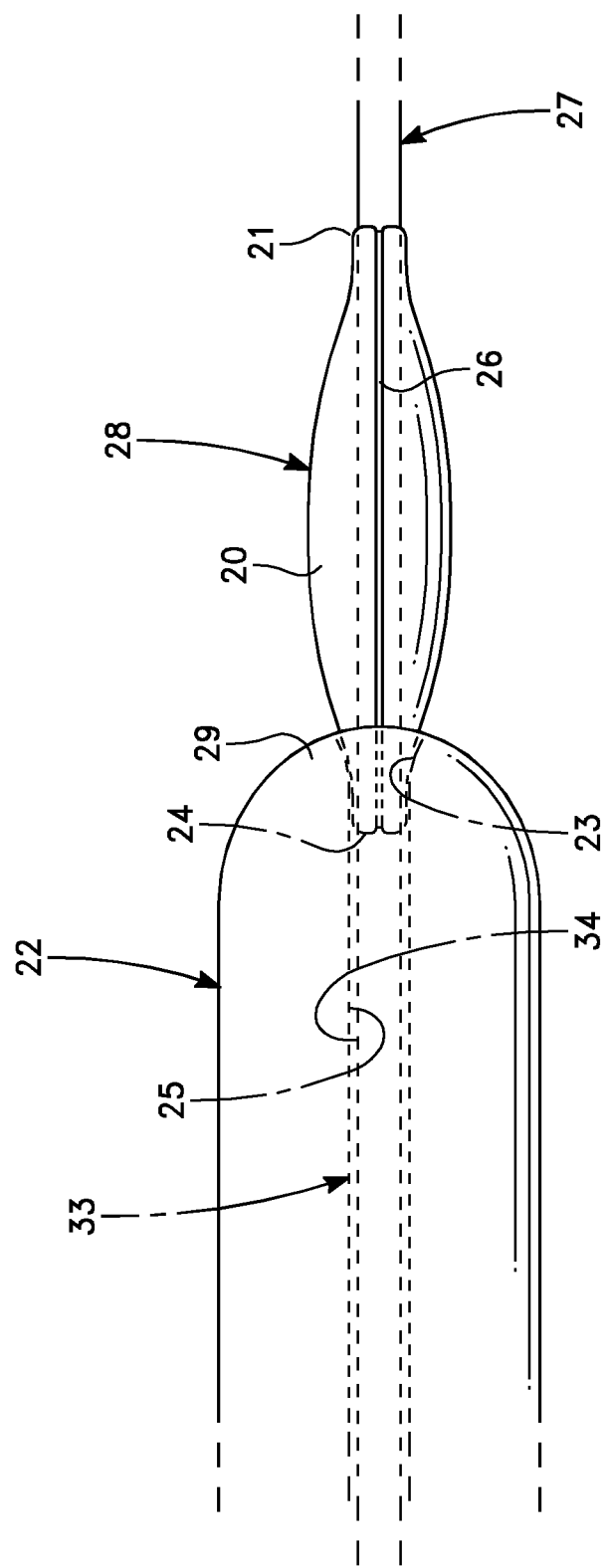
FIG. 4 is a side elevation view of the covering of FIG. 2 in place on a human penis fitted with a catheter. The bandage wraps around the proximal portion of the catheter, through the urethral meatus and a short distance into the urethra.

FIGS. 2A, 2B and 4 show a plan view of a second, exemplary embodiment of a therapeutic covering 28 that may be placed over, and partly inside of, a human penis 22 fitted with a catheter 27 that extends from a human's bladder (not shown) through, and beyond the opening 23 from the penis glans 29. This embodiment, too, is formed from a generally flat, square/rectangular shape bandage material.

FIG. 4 shows end 21 of covering 28 wrapped over/around catheter 27, at covering 28's distal end. Covering 28's body 20 extends from covering end 21 to, and into the opening 23 in penis 22, at tapering covering end 24. As FIG. 4 shows, tapering end 24 has a generally/substantially rounded cross sectional profile, and a cross sectional size appropriate to fit inside penis 22 between the inner surface 25 of penis urethra 33, and the external surface 34 of catheter 27 inside penis 22. Adhesive strips 26 holds covering 28 closed, along the periphery of covering 28's longitudinal juncture over/around catheter 27.

Inner/outer surfaces 35 of covering 28 are soft, padded and, optionally, coated or impregnated with lubricant(s) and/or disinfectants over at least some of the areas that will be in contact with penile tissues when/while covering 28 is in place on/inside of penis 22. These same areas may be lubricated and/or medicated over at least part of the covering surfaces inside the penis along the external surface of the catheter.

Figure 5:
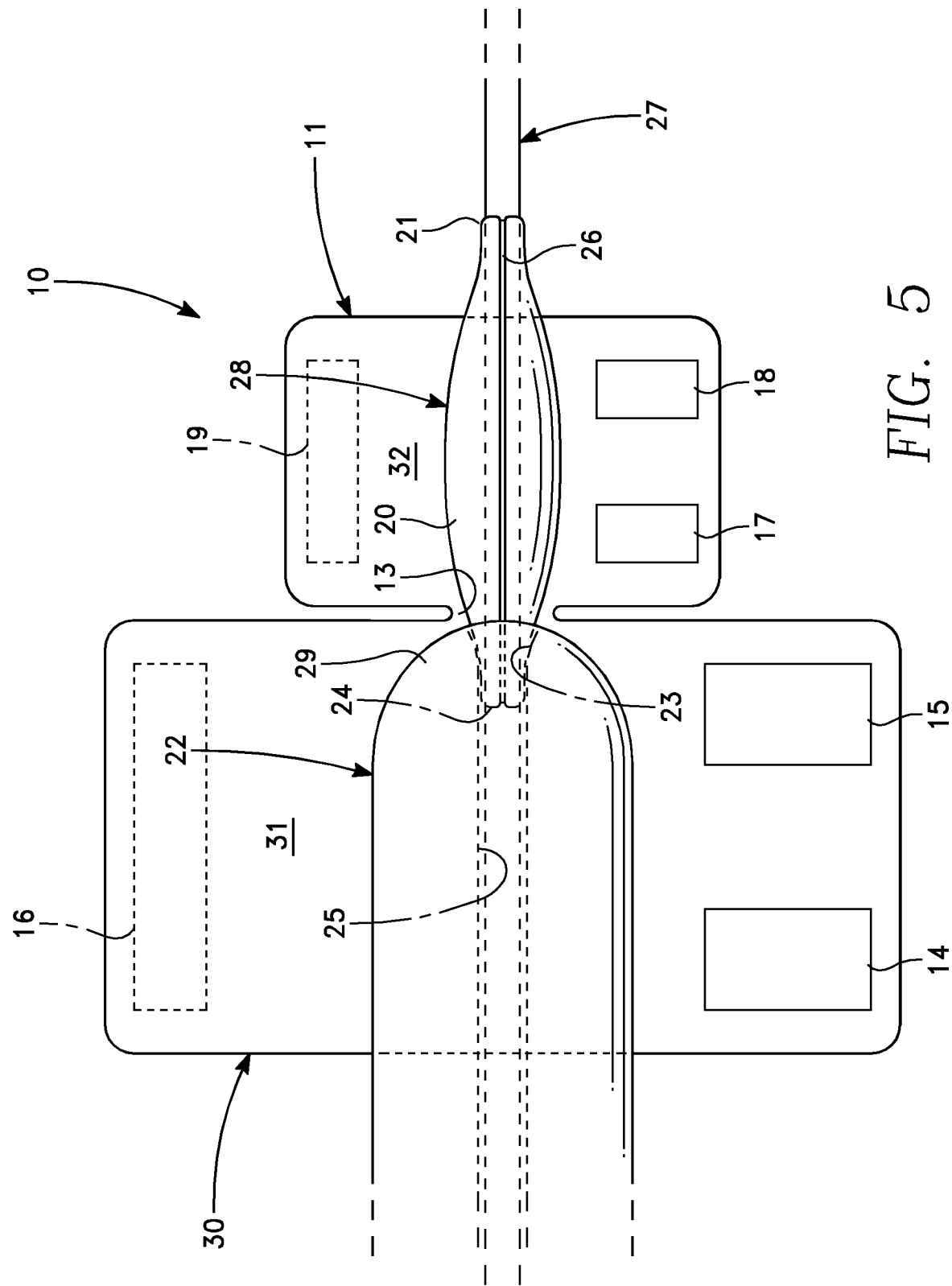
FIG. 5 is a side elevation view of the coverings of FIGS. 1 and 2 placed alongside a human penis fitted with a catheter that extends from a human's bladder through, and beyond the urethral meatus.

FIG. 5 shows coverings 10 and 28 used together in placement placed over, and partly inside of, a human penis 22 fitted with a catheter 27 that extends from a human's bladder (not shown) through, and beyond the opening 23 from the penis glans 29. Here, covering 28 is placed over/inside penis 22 as described herein above, and secured in place as described above in connection with FIGS. 2 and 4. Then, covering 10 is placed over/around covering 28, and penis 22, where catheter 27 protrudes from opening 23 in penis 22. Together, coverings 28 and 10 cover, protect and cushion/medicate/lubricate the abrasion-vulnerable urethral meatus 23 and glans 29.

Whether a person/wearer uses covering 10 alone, covering 28 alone, or coverings 10 and 28 together, the flow of urine through catheter 27 from the wearer's bladder through catheter 27 to a urine collector, such as a pouch, is unimpeded.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A substantially planar, therapeutic, one piece covering for use after insertion of a tubular catheter through a human's urethra into said human's bladder, said covering comprising a first, substantially planar first surface, and a second, substantially planar second surface, said covering being adapted to be placed over an interface between the opening at a distal end of a human penis, and an external surface of said tubular catheter, said tubular catheter extending through and beyond the meatus of said penis and through and beyond said opening, and where said covering wraps around, and is adapted to fasten to said interface, covering and cushioning said interface.

2. The therapeutic covering of claim 1, wherein the covering surfaces of said covering that are in contact with penile and glans tissues are soft, non-abrasive, and optionally, lubricated, impregnated with antiseptic, or padded to promote comfort/minimize penile tissue damage.

3. A substantially planar, therapeutic one piece covering for use after insertion of a tubular catheter through a human's urethra into said human's bladder, said covering comprising a first, substantially planar first surface, and a second, substantially planar second surface, said covering being adapted to be placed partly inside of, an interface between the opening at a distal end of a human penis, and an external surface of said tubular catheter that extends through and beyond the meatus of said penis and through and beyond said opening, said covering tapering at one end, and substantially conforming to an external surface of said catheter such that said covering can pass over the catheter's external surface into the urethra of said penis a short distance, to lie inside said urethra between the external surface of the catheter, and an internal surface of said urethra.

4. A substantially planar therapeutic one piece covering for use after insertion of a tubular catheter through a human's urethra into said human's bladder, comprising a first, substantially planar first surface on a first side of said covering, and a second, substantially planar second surface on a second side of said covering, said covering being adapted to be wrapped around, and fasten over, an interface between the glans of a human penis that includes a urethra having an internal surface, and said tubular catheter, said catheter extending through and beyond the opening of said glans, said covering cushioning said catheter/glans opening interface.

5. A substantially planar therapeutic one piece covering for use after insertion of a tubular catheter through a human's urethra into said human's bladder, comprising a first, substantially planar first surface on a first side of said covering, and a second, substantially planar second surface on a second side of said covering, said covering including a portion adapted to extend inside the urethra of a human penis, and around said tubular catheter, said catheter extending through and beyond the opening of the glans of said penis.

6. The therapeutic covering of claim 5, wherein said covering tapers at one end, when in place over said interface, to a size/shape that is adapted to extend over the catheter's external surface into the urethra of said penis a short distance, to lie inside said urethra between the external surface of the catheter, and the internal surface of said urethra.

7. The therapeutic covering of claim 6, wherein another portion of said covering outside the urethra wraps over, or around the external surface of said catheter tube that protrudes from said opening.

8. A substantially planar flexible one-piece covering for use after insertion of a tubular catheter through a human's urethra into said human's bladder, comprising a first side and a second side, wherein said first side includes a soft, non-abrasive, lubricated surface that is optionally impregnated with an antiseptic, and wherein said covering includes a first portion connected to a second portion by a neck positioned between said first portion and said second portion, said first and second portions being of sufficient size and shape to wrap over and around a human penis that includes a glans having a distal opening and that connects to a bladder of a human, and is fitted with a catheter that extends from said bladder of a human through said human's urethra and beyond the opening in the glans of said penis.

\* \* \* \* \*